US005854005A

United States Patent [19]

Coller

[11] Patent Number: 5,854,005
[45] Date of Patent: *Dec. 29, 1998

[54] PLATELET BLOCKADE ASSAY

[75] Inventor: Barry S. Coller, New York, N.Y.

[73] Assignee: Mount Sinai School of Medicine, New York, N.Y.

[ * ] Notice: The term of this patent shall not extend beyond the expiration date of Pat. No. 5,763,199.

[21] Appl. No.: 754,773

[22] Filed: Nov. 20, 1996

Related U.S. Application Data

[63] Continuation-in-part of Ser. No. 315,026, Sep. 29, 1994, Pat. No. 5,763,199.
[51] Int. Cl.$^6$ ........................ G01N 33/546; G01N 33/552
[52] U.S. Cl. ........................ 435/7.21; 435/7.24; 436/69; 436/527; 436/533
[58] Field of Search ................................ 435/7.21, 7.24, 435/975; 436/69, 533, 527

[56] References Cited

U.S. PATENT DOCUMENTS

| 5,114,842 | 5/1992 | Plow et al. | 424/85.8 |
| 5,196,309 | 3/1993 | Ginsberg | 435/7.21 |
| 5,246,832 | 9/1993 | Michelson et al. | 435/7.2 |
| 5,266,462 | 11/1993 | Hemker et al. | 435/13 |
| 5,275,812 | 1/1994 | Gold et al. | 424/85.8 |
| 5,284,751 | 2/1994 | Frelinger, III et al. | 435/7.21 |
| 5,306,632 | 4/1994 | Anderson et al. | 435/180 |
| 5,427,913 | 6/1995 | Shaw et al. | 435/7.21 |
| 5,455,228 | 10/1995 | Coller et al. | 514/17 |
| 5,523,238 | 6/1996 | Varon et al. | 436/69 |

FOREIGN PATENT DOCUMENTS

| 0 165 681 | 12/1985 | European Pat. Off. . |
| 0 397 119 | 11/1990 | European Pat. Off. . |
| WO 89/00200 | 1/1989 | WIPO . |
| WO 92/08982 | 5/1992 | WIPO . |
| WO 94/12664 | 6/1994 | WIPO . |
| WO 94/22018 | 9/1994 | WIPO . |
| WO 95/27209 | 10/1995 | WIPO . |

OTHER PUBLICATIONS

Coller et al, Blood, vol. 84, No. 10, Suppl. 1, 474A, 1994.

Excerpt from Dorland's Illustrated Medical Dictionary, [1st]–ed., 1985 by W.B. Saunders Company, 26th Ed., p. 1364.

Kleiman, N.S., "Profound Inhibition of Platelet Aggregation With Monoclonal Antibody 7E3 Fab After Thrombolytic Therapy," *JACC*, vol. 22, No. 2, (Aug. 1993):381–9.

Ware, J. A. et al, "Platelet Morphology, Biochemistry, and Function," *Hemostasis and Thrombosis*, Chapter 119, Part X:1161–1201 (undated).

Coller, B. S., "Interaction of Normal, Thrombasthenic, and Bernard–Soulier Platelets with Immobilized Fibrinogen: Defective Platelet–Fibrinogen Interaction in Thrombasthenia," *Blood*, 55(2):169–178 (Feb. 1980).

Coller, B. S., "A Murine Monoclonal Antibody that Completely Blocks the Binding of Fibrinogen to Platelets Produces a Thrombasthenic–like State in Normal Platelets and Binds to Glycoproteins IIb and/or IIIa," *J. Clin. Invest.*, 72:325–338, The American Society for Clinical Investigation, Inc. (1983).

Coller, B. S. et al., "Thrombin Receptor Activating Peptides: Importance of the N–Terminal Serine and its Ionization State as Judged by pH Dependence, Nuclear Magnetic Resonance Spectroscopy, and Cleavage by Aminopeptidase M," *Biochemistry*, 31(47):11713–11720 (1992).

Coller, B. S., et al., "Substituting Isoserine for Serine in the Thrombin Receptor Activation Peptide SFLLRN Confers Resistance to Aminopeptidase M–induced Cleavage and Inactivation," *The Journal of Biologial Chemistryt*, 268(28):20741–20743 (1993).

Peerschke, E., "Glycoprotein IIb and IIIa Retention on Fibrinogen–Coated Surfaces After Lysis of Adherent Platelets," *Blood*, 82(11);3358–3363, (Dec. 1, 1993).

Carr, M. E. et al., "Glycoprotein IIb/IIIa Blockade Inhibits Platelet–Mediated Force Development and Reduces Gel Elastic Modulus," *Thrombosis and Haemostasis, Journal of the International Society on Thrombosis and Haemostasis*, 73(3):499–505 (1995).

Santoro, S. A. and Lawing W. J., Jr., "Competition for Related but Nonidentical Binding Sites on the Glycoprotein IIb–IIIa Complex by Peptides Derived from Platelet Adhesive Proteins," *Cell*, 48:867–873 (Mar. 1987).

Sheu J. R., et al., Triflavin, an Arg–Gly–Asp Containing Snake Venom Peptide, Inhibits Aggregation of Human Platelets Induced by Human Hepatoma Cell Line, *Thrombosis Research* 66:679–691 (1992).

Plow, E. F., et al. "The Effect of Arg–Gly–Asp–Containing Peptides on Fibrinogen and Von Willebrand Factor Binding to Platelets," *Proc. Natl. Acad. Sci. USA*, 82:8057–8061 (Dec. 1985).

Beer, et al., "Immobilized Arg–Gly–Asp (RGD) Peptides of Varying Lengths as Structural Probes of the Platelet Glycoprotein IIb/IIIa Receptor," *Blood*, 79:117–128 (1992).

(List continued on next page.)

*Primary Examiner*—David Saunders
*Attorney, Agent, or Firm*—Heller Ehrman White & McAuliffe

[57] ABSTRACT

The present invention is an assay for determining glycoprotein IIb/IIIa receptor blockade in whole blood. Agglutinization of small polymeric beads coated with a glycoprotein IIb/IIIa ligand such as fibrinogen results when the beads are contacted with whole blood containing platelets with glycoprotein IIb/IIIa receptors that are not blocked. Failure to agglutinate indicates that blockade of the GPIIb/IIIa receptors has been achieved. In a preferred embodiment, the addition of a thrombin receptor activator results in an assay that is rapid and convenient enough to be performed at the bedside and that results in agglutination of the small polymeric beads within a convenient, known period of time if the glycoprotein IIb/IIIa receptors are not blocked.

35 Claims, No Drawings

OTHER PUBLICATIONS

Vu, et al., "Molecular Cloning of a Functional Thrombin Receptor Reveals a Novel Proteolytic Mechanism of Receptor Activation," *Cell*, 64:1057–1068 (1991).

Coller, et al., "Collagen–Platelet Interactions: Evidence for a Direct Interaction of Collagen With Platelet GPIa/IIa and an Indirect Interaction With Platelet GPIIb/IIIa Mediated by Adhesive Proteins," *Blood*, 74:182–192 (1989).

Charo, et al., "Inhibition of Fibrinogen Binding to GP IIb–IIIa by a GP IIIa Peptide," *J. Biol. Chem.*, 266:1415–1421 (1991).

Coller, et al., "Studies of Activated GPIIb/IIIa Receptors on the Luminal Surface of Adherent Platelets," *J. Clin. Invest.*, 92:2796–2806 (1993).

Kamiyama, et al., Inhibition of platelet GPIIb/IIIa binding to fibrinogen by serus factors: Studies of circulating immune complexes and platelet antibodies in patients with hemophilia, immune thrombocytopenic purpura, human immunodeficiency virus–related immune thrombocytopenic purpura, and systemic lupus erythematosus, *J. Lab. Clin. Med.*, 117:209–217 (1991).

Pfueller, et al., "Role of Plasma Proteins in the Interaction of Human Platelets with Particles," *Thrombosis Research*, 12:979–990.

Coller, et al., "Thromboerythrocytes: In Vitro studies of a Potential Autologous, Semi–artificial Alternative to Platelet Transfusions," *J. Clin. Invest.*, 89:546–555 (1992).

Califf, et al., "Use of a Monoclonal Antibody Directed Against the Platelet Glycoprotein IIb/IIIa Receptor in High–Risk Coronary Angioplasty," *N. Engl. J. Med.*, 330:956–961 (1994).

Coller, et al., "Monoclonal Antibodies to Platelet Glycoprotein IIb/IIIa as Antithrombotic Agents," *Ann. NY Acad. Sci.*, 614:193–213 (1991).

Lavee, et al., "The effect of transfusion of fresh whole blood versus platelet concentrates after cardiac operations," *J. Thorac. Cardiovasc. Surg.* 97:204–212 (1989).

Chrono–Log brochure, "Chrono–Log Aggregation Systems Improve Platelet Function Studies" (undated).

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:1:

```
Ser  Phe  Leu  Leu  Arg  Asn  Pro  Asn  Asp  Lys  Tyr  Glu  Pro  Phe
1                   5                        10
```

( 2 ) INFORMATION FOR SEQ ID NO:2:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:2:

```
Ser  Phe  Leu  Leu  Arg  Asn  Pro  Asn  Asp  Lys  Tyr
1                   5                        10
```

( 2 ) INFORMATION FOR SEQ ID NO:3:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( v ) FRAGMENT TYPE: N-terminal ( i x ) FEATURE:
        ( A ) NAME/KEY: Modified-site
        ( B ) LOCATION: 1
        ( D ) OTHER INFORMATION: /product="OTHER"
        / note= ""xaa=isoserine""

( x i ) SEQUENCE DESCRIPTION: SEQ ID NO:3:

Xaa  Phe  Leu  Leu  Arg  Asn
    1                       5

( 2 ) INFORMATION FOR SEQ ID NO:4:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:4:

Ser  Phe  Leu  Leu  Arg  Asn
    1                       5

( 2 ) INFORMATION FOR SEQ ID NO:5:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( i x ) FEATURE:
        ( A ) NAME/KEY: Modified-site
        ( B ) LOCATION: 1
        ( D ) OTHER INFORMATION: /product="OTHER"
        / note= ""xaa=isoserine""

( x i ) SEQUENCE DESCRIPTION: SEQ ID NO:5:

Xaa  Phe  Leu  Leu  Arg  Asn  Pro  Asn  Asp  Lys  Tyr
    1                       5                           10

( 2 ) INFORMATION FOR SEQ ID NO:6:

( i ) SEQUENCE CHARACTERISTICS:
        ( A ) LENGTH: 14 amino acids (B) TYPE: amino acid
(C) STRANDEDNESS: single
(D) TOPOLOGY: unknown (ii) MOLECULE TYPE: peptide (iii) HYPOTHETICAL: NO (iv) ANTI-SENSE: NO (v) FRAGMENT TYPE: N-terminal (ix) FEATURE:
(A) NAME/KEY: Modified-site
(B) LOCATION: 1
(D) OTHER INFORMATION: /product="OTHER"
/ note= ""xaa=isoserine""

(xi) SEQUENCE DESCRIPTION: SEQ ID NO:6:

Xaa Phe Leu Leu Arg Asn Pro Asn Asp Lys Tyr Glu Pro Phe
1               5                   10

(2) INFORMATION FOR SEQ ID NO:7:

(i) SEQUENCE CHARACTERISTICS:
(A) LENGTH: 5 amino acids
(B) TYPE: amino acid
(C) STRANDEDNESS: single
(D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:7:

Ser Phe Leu Leu Arg
1               5

(2) INFORMATION FOR SEQ ID NO:8:

(i) SEQUENCE CHARACTERISTICS:
(A) LENGTH: 5 amino acids
(B) TYPE: amino acid
(C) STRANDEDNESS: single
(D) TOPOLOGY: unknown (ii) MOLECULE TYPE: peptide (iii) HYPOTHETICAL: NO (iv) ANTI-SENSE: NO (v) FRAGMENT TYPE: N-terminal (ix) FEATURE:
(A) NAME/KEY: Modified-site
(B) LOCATION: 1
(D) OTHER INFORMATION: /product="OTHER"
/ note= ""xaa=isoserine""

(xi) SEQUENCE DESCRIPTION: SEQ ID NO:8:

Xaa Phe Leu Leu Arg
1               5

(2) INFORMATION FOR SEQ ID NO:9:

(i) SEQUENCE CHARACTERISTICS:
(A) LENGTH: 4 amino acids
(B) TYPE: amino acid
(C) STRANDEDNESS: single ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( i x ) FEATURE:
            ( A ) NAME/KEY: Modified-site
            ( B ) LOCATION: 1
            ( D ) OTHER INFORMATION: /product="OTHER"
                / note= "Xaa=Gly(1-20)"

( x i ) SEQUENCE DESCRIPTION: SEQ ID NO:9:

Xaa  Arg  Gly  Asp
        1

( 2 ) INFORMATION FOR SEQ ID NO:10:

( i ) SEQUENCE CHARACTERISTICS:
            ( A ) LENGTH: 5 amino acids
            ( B ) TYPE: amino acid
            ( C ) STRANDEDNESS: single
            ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( i x ) FEATURE:
            ( A ) NAME/KEY: Modified-site
            ( B ) LOCATION: 1
            ( D ) OTHER INFORMATION: /product="OTHER"
                / note= "Xaa=Gly(9-11)"

( x i ) SEQUENCE DESCRIPTION: SEQ ID NO:10:

Xaa  Arg  Gly  Asp  Phe
        1                   5

PLATELET BLOCKADE ASSAY

CROSS REFERENCES TO RELATED APPLICATION

This application is a continuation-in-part of U.S. Ser. No. 08/315,026, filed Sep. 29, 1994, now U.S. Pat. No. 5,763,199, the disclosure of which is incorporated by reference herein.

BACKGROUND OF THE INVENTION

New agents that block the platelet glycoprotein IIb/IIIa (GPIIb/IIIa) receptor are being developed for use as antithrombotic agents in medical applications such as angioplasty and atherectomy. The doses of these agents required to achieve equivalent antiplatelet effects are likely to differ as a function of platelet count, glycoprotein IIb/IIIa (GPIIb/IIIa) surface density, and individual variations in drug pharmacokinetics. In fact, in one [(Simoons et al. Circulation, 89:596, (1994)) study, a patient with a platelet count greater than 900,000/$\mu$l, who received a standard dose of c7E3 Fab had virtually no antithrombotic effect. Since platelet counts within the normal range differ by more than 2-fold (150,000/$\mu$l–350,000/$\mu$l), and platelet GPIIb/IIIa density per platelet also differs by about 2-fold, there may be as much as a four-fold difference in the total number of GPIIb/IIIa receptors requiring blockade even within the normal population. Little is known about individual differences in the pharmacokinetics of different GPIIb/IIIa blocking agents, but it is reasonable to expect variation based on renal function and perhaps other factors that act on low molecular weight compounds.

Several assays are currently available for evaluating GPIIb/IIIa receptor blockade, including platelet aggregation, and in the case of c7E3, either radiolabeled 7E3 binding or flow cytometry. These assays are time consuming, require special equipment and require extensive standardization and so are not suitable for bedside monitoring.

It would be desirable, therefore, to have a rapid and simple assay to assess the extent of receptor blockade in an individual. In the setting of angioplasty, it would be desirable to have a GPIIb/IIIa receptor assay conducted at the same time as determination of activated clotting time (ACT), which is an indicator of extent of heparinization, that would indicate when the desired level of blockade had been achieved and that the patient was ready to undergo the angioplasty. During chronic infusions, periodic monitoring may also be desirable. Further, in certain circumstances (prior to surgery or an invasive procedure) it may be desirable to rapidly determine whether the effect of the GPIIb/IIIa blocking drug has worn off.

SUMMARY OF THE INVENTION

The present invention relates to a method of determining the level of residual unblocked glycoprotein IIb/IIIa receptors in whole blood and, thus, the ability of the individual's platelets to undergo aggregation. Thus, the method refers to a method of determining whether an individual has reduced ability to form platelet thrombi. The present invention also relates to a kit comprising the reagents for carrying out the assay.

The method comprises a first step in which blood is withdrawn from an individual being assessed for GPIIb/IIIa blockade and is mixed with an anticoagulant. The whole blood/anticoagulant mixture is combined with a buffer which maintains the pH and the salt concentration of the mixture at levels suitable for platelet aggregation, and with a GPIIb/IIIa ligand immobilized on a solid surface. The ligand is immobilized on the solid surface such that platelet mediated agglutination of the solid surface in the presence of platelets with unblocked GPIIb/IIIa is detectable. The resulting mixture is then agitated for a period of time that is sufficient to allow unblocked platelet GP IIb/IIIa receptors to bind with the GP Ib/IIIa receptor ligand. The absence of agglutination indicates that the GPIIb/IIIa receptors are blocked. In one aspect the solid surface is a small polymeric bead on which the ligand is immobilized at a density to allow the platelets to agglutinate the beads in the presence of unblocked GPIIb/IIIa receptor. Platelet aggregation potential is determined by bead agglutination. The absence of bead agglutination indicates that the GPIIb/IIIa receptors are blocked and the individual has reduced ability to form platelet thrombi. Optionally, a thrombin receptor activating peptide can be added, which causes the beads to agglutinate more quickly and causes agglutination to occur within a defined period of time. The amount of thrombin activating peptide can be adjusted so that agglutination occurs within a short time, such as two minutes to five minutes if blockade of GPIIb/IIIa receptors is less than 80%. The absence of agglutination indicates that the individual will have impaired platelet aggregation which generally correlates with prolonged bleeding times and reduced ability to form platelet thrombi. Alternatively, less thrombin receptor activating peptide can be used, such that agglutination will occur within a short period of time, such as two to five minutes, if blockade of GPIIb/IIIa receptors is less than about 50%. This indicates that the individual will have a normal or near normal bleeding time.

The assay of the present invention has the advantage that it can be conveniently performed at the time of need, such as when a surgical procedure is being performed or about to be performed, in a matter of minutes without the need for expensive equipment or highly trained medical personnel. Such an assay has the further advantage that it is rapid enough to be used to indicate whether a patient undergoing antiplatelet therapy has achieved a sufficiently high level of GP IIb/IIIa blockade to proceed with a surgical procedure such as angioplasty, in which thrombosis must be avoided. In the event that a patient undergoing antiplatelet therapy requires invasive surgery, the assay is also useful to determine the extent to which the GP IIb/IIIa blocking drug is acting and, thus, whether a platelet transfusion is needed to reverse the effect.

The present invention also relates to a kit that comprises the reagent for carrying out the assay of the present invention. The present invention further relates to a method of diagnosing an individual with Glanzmann thrombasthenia or with the thrombocytopenia using the asset of the present invention.

DETAILED DESCRIPTION OF THE INVENTION

GP IIb/IIIa receptor proteins, which are found on the cell surface of platelets, play a central role in thrombosis, i.e., coagulation (clotting of blood. The binding of fibrinogen and perhaps other macromolecular ligands to GPIIb/IIIa leads to platelet aggregation and is consequently an essential step in the cascade that leads to platelet thrombosis formation and coagulation.

A large enough deficiency in the number of unblocked GPIIb/IIIa receptor proteins in an individual results in a decreased ability of platelets to aggregate, thus resulting in reduced ability to form platelet thrombi and abnormally long bleeding times. For example, blockade of about 80% or more of an individual's GPIIb/IIIa receptors, for example by the administration of a GPIIb/IIIa receptor blocking agent such as monoclonal antibody c7E3 Fab, abolishes platelet aggregation and prolongs the bleeding times (period of time in which the individual will bleed from a wound before platelet thrombosis formation stops the bleeding), often to times greater than thirty minutes. Such individuals have an impaired ability to thrombose, i.e., to form blood clots. Certain diseases also result in decreased levels of unblocked GPIIb/IIIa receptors. For example, individuals who are homozygous for Glanzmann thrombasthenia have virtually no GPIIb/IIIa receptor proteins on their platelet cell surfaces and also have prolonged bleeding times (Coller et al. Ann. N.Y. Acad. Sci 614:193 (1993). In addition, individuals who are severely thrombocytopenic, i.e., have platelet counts below 100,000 platelets/μl, have similar prolonged bleeding times. However, platelet aggregation is unaffected or minimally affected in individuals until about 40–50% of GPIIb/IIIa receptors are blocked and bleeding times are normal until as many as about 60% of GPIIb/IIIa receptors are blocked. Levels of GPIIb/IIIa blockade up to about 80% result in mild to moderate abnormalities in platelet aggregation and bleeding times (Coller et al. Ann. N.Y. Acad. Sci 614:193 (1993)). Consistent with these figures is the observation that individuals who are heterozygous for Glanzmann thrombasthenia and who have only 50–60% of the normal numbers of GPIIb/IIIa receptors show normal bleeding times. Consequently, the ability of the blood of an individual to undergo platelet aggregation and coagulate is dependent on the number of unblocked GPIIb/IIIa receptors.

One embodiment of the present invention is a method of assessing whether an individual will have severely impaired ability to form platelet thrombi or impaired platelet aggregation due to blockade of about 80% or more of the GPIIb/IIIa receptors or to a similar deficiency in the number of GPIIb/IIIa receptors. An individual with a blockade of 80% or more of the GPIIb/IIIa receptors will have prolonged bleeding times, i.e. bleeding times of greater than about thirty minutes, an impaired ability to form platelet thrombi and impaired platelet aggregation. The method comprises determining whether greater than 80% of the GP IIb/IIIa receptors are blocked in whole blood. Blockade of 80% or more of GP IIb/IIIa receptors in whole blood is determined by withdrawing blood from an individual being assessed for GPIIb/IIIa blockade and mixing the blood with an anticoagulant. The whole blood/anticoagulant mixture is then combined with 1) a buffer that is capable of maintaining the pH and salt concentrations of the blood at levels suitable for platelet aggregation and 2) a GP IIb/IIIa ligand immobilized on a solid surface such that platelet mediated agglutination of the solid surface is detectable when the solid surface is combined with platelets having unblocked GPIIb/IIIa receptors. The resulting mixture is then agitated for a period of time that is sufficient to allow unblocked platelet GP IIb/IIIa receptors to bind with the GP IIb/IIIa receptor ligand. The absence of platelet aggregation indicates that more than about 80% of the GPIIb/IIIa receptors are blocked. The absence of platelet mediated agglutination of the solid surface also indicates that the individual will have reduced platelet aggregation, a prolonged bleeding time and reduced ability to form thrombi. Platelet mediated agglutination of the solid surface indicates that less than about 80% of the GPIIb/IIIa receptors are blocked. Preferably, the solid surface is a small polymeric bead. The GPIIb/IIIa ligand must be immobilized at a sufficient density on the surface of the beads so that the beads can agglutinate in the presence of platelets with GPIIb/IIIa receptors that are not blocked. The absence of agglutination indicates blockade or absence of GPIIb/IIIa receptors.

As used herein, GPIIb/IIIa receptors are blocked when a drug, peptide, monoclonal antibody or small organic molecule binds to, complexes with or interacts with the GPIIb/IIIa receptor such that a natural ligand of the GPIIb/IIIa receptor, for example fibrinogen, cannot bind to the GPIIb/IIIa receptor.

Blood can be drawn from the individual being assessed for GPIIb/IIIa receptor blockade by any number of known techniques. Preferably, the blood is drawn into a Vacutainer or other closed tube to protect the individual who is drawing the blood from blood-borne infectious agents such as the hepatitis B virus or the HIV virus. The whole blood is then mixed with an anticoagulant. This can be carried out, for example, by drawing the blood into a tube containing anticoagulant or by adding anticoagulant to drawn blood. A sufficient amount of anticoagulant is used to prevent coagulation of the whole blood. Suitable anticoagulants include citrate, oxalate, ACD-A, heparin, hirudin or other antithrombin agent. A preferred anticoagulant is citrate. The final citrate concentration in the whole blood ranges from 0.3% to about 0.5% of the blood, preferably about 0.4%. Whole blood to which a sufficient amount of anticoagulant has been added to prevent coagulation is referred to as "anticoagulated blood".

The anticoagulated blood is mixed in an assay tube with a buffer and a suitable amount of small polymeric beads on whose surface a ligand that binds to the platelet GPIIb/IIIa receptor has been immobilized to produce an anticoagulated blood-bead mixture. The ligand is immobilized at a density sufficient to allow the beads to agglutinate in the presence of platelets with GPIIb/IIIa receptors that are not blocked.

A suitable buffer is capable of maintaining the pH and salt concentration of the blood within a range suitable for platelet aggregation. Suitable pH levels are about 6.6–8.2 and is preferably about 7.4. The buffer may be added to the blood sample either as a solution or solely as the buffering composition and salts. A suitable buffer comprises a concentration of a buffering composition such as HEPES, Tris or others that maintain the pH of the blood within the range suitable for platelet aggregation, as defined above. HEPES is a preferred buffer and is present generally at a concentration of 0.01M. A suitable buffer also maintains the salt concentration of the blood within a range suitable for platelet aggregation. Consequently, the buffer contains a concentration of one or more salts, such as NaCl, that maintain the electrolytic balance of the blood within a range suitable for platelet aggregation. Suitable concentrations of NaCl in the buffer are between 0.10M and 0.20M, but typically 0.15M. In addition, salts such as $CaCl_2$ are required for binding between the GPIIb/IIIa receptor and the GPIIb/IIIa receptor ligand such as fibrinogen. Suitable buffer concentrations of $CaCl_2$ range between about 0.1 mM and about 1.0 mM, and are preferably about 0.5 mM.

A GPIIb/IIIa ligand is a small organic molecule, polypeptide, protein, monoclonal antibody or nucleic acid that binds, complexes or interacts with GPIIb/IIIa receptors on the platelet surface. The platelet mediated agglutination of the solid surface results when the GPIIb/IIIa receptors on the surface of platelets bind, complex or interact with GPIIb/IIIa ligands bound to the solid surfaces. Suitable GPIIb/IIIa ligands include fibrinogen, monoclonal antibody 1OES (Coller et al. J. Clin. Invest. 72:325 (1983), deposited with the American Type Culture Collection (ATCC), 12301 Parklawn Drive, Rockville, Md., Accession No. 1006088, monoclonal antibody c7E3 (The EPIC Investigators, *N.E. Journal of Med.,* 330:956 (1994), other monoclonal antibodies, von Willebrand factor, fibronectin, vitronectin and ligands that comprise an arginine-glycine-aspartic (RGD) acid sequence or other peptides or peptidomimetics that mimic this sequence (Cook et al. *Drugs of the Future* 19:135 (1994)). The RGD functional equivalent ligands include gamma chain peptides, peptidomimetic and cyclic peptides with an activity that is about the same as an RGD ligand.

A solid surface is any surface onto which a GPIIb/IIIa ligand can be immobilized such that platelet mediated agglutination of the solid surface is detectable when the solid surface is combined with platelets having unblocked GPIIb/IIIa receptors. Typically, the ligand is immobilized on the surface at a density such that platelet mediated agglutination of the solid surface can occur by binding of the platelet GPIIb/IIIa receptor with the immobilized ligand. The ligand is immobilized on the solid surface by covalent binding, complexing or adsorption, such that the ligand is capable of binding to GPIIb/IIIa receptors. Suitable solid surfaces include glass (for example, glass particles or test tubes), plastic, or small polymeric beads. Small polymeric beads are preferred. The detection of platelet mediated agglutination of the solid surface can be accomplished visually or by means of a magnification aid. Preferably, platelet binding to the solid surface is detected by observing some change in the solid surface which occurs as a consequence of platelet binding, for example, agglutination of small polymeric beads or plastic or glass microparticles.

A small polymeric bead, as used herein is any polymeric microparticle a GPIIb/IIIa receptor ligand can be covalently bound to or adsorbed on. The polymeric microparticles can be virtually any shape, but are generally spherical with uniform diameters ranging from about 0.1 $\mu$m to about 10 $\mu$m in diameter. Preferred diameters are from about 1.0 $\mu$m to about 6.0 $\mu$m in diameter. For example, the polymeric microparticle may be polymerized acrylonitrile 1–3 $\mu$m beads with N-hydroxysuccinimide ester groups on their surface (e.g., Matrex 102 beads from Amicon Corporation) (Coller, Blood, 55:169 (1980)). The N-hydroxysuccinimide ester groups allow coupling of the N-terminus of the peptide, protein or monoclonal antibody to the surface of the bead (see example 2). Alternatively, the microparticle can be carboxylated polystyrene 3–6 $\mu$m beads (Polysciences Inc.). The surface carboxyl groups of this bead can be coupled to the N-terminus of the protein, peptide or monoclonal antibody by means of a carbodiimide coupling (see Example 1). The beads may be colored to render the results of the agglutination reaction easier to interpret.

In carrying out the method of the present invention, 10 $\mu$l–200 $\mu$l of anticoagulated blood, 10 $\mu$l–200 $\mu$l of buffer solution and 1 $\mu$l–50 $\mu$l of small beads are mixed in the second step of the present invention. In one embodiment, about 50 $\mu$l of anticoagulated blood, about 50 $\mu$l of buffer solution, and about 5 $\mu$l of small beads are used. Alternatively, the mixture can be scaled up or down, as long as the ratio of the components used remain within the limits described above.

As discussed previously, the GPIIb/IIIa receptor ligand can also be a ligand comprising an arginineglycine-aspartic acid sequence, or mimic thereof, which is covalently bound to the solid surface through a suitable spacer. Examples of suitable ligands are disclosed in Beer et al., *Blood* 79:117 (1992), the contents of which are incorporated in their entirety herein by reference. Suitable GPIIb/IIIa receptor ligands include the peptide (glycine)$_n$-arginine-glycine-aspartic wherein n is an integer from 2–20 (SEQ ID NO:9). The polyglycine portion of the ligand is the spacer and is covalently bound to the surface of the polymeric bead at the N-terminal amino group. While the RGD sequence may participate in the binding to platelets, a gamma chain sequence forming a molecular mimic of the RGD sequence may be more important in the binding of fibrinogen to platelets (Coller, Platelet Morphology, Biochemistry, and Function, 1175). Divalent cations such as calcium, magnesium, and manganese are required for the binding of all GPIIb/IIIa ligands, and each ligand differs subtly with respect to the preferred cation. The competence of activating agents also varies among ligands (Id. at 1175, 76). Optionally, an additional amino acid or oligopeptide which does not significantly interfere with the binding of arginine-glycine-aspartic acid to the GPIIb/IIIa receptor may be bound to the C-terminus of aspartic acid by means of a peptide bond. In one embodiment, the GPIIb/IIIa receptor ligand comprises (Glycine)$_{9-11}$-arginine-glycine-aspartic acid-phenylalanine (SEQ ID NO:10). Alternatively, the spacer portion of the ligand can comprise any moiety which causes the arginine-glycine-aspartic acid sequence to extend out from the surface of the microparticle sufficiently to allow binding between the ligand and GPIIb/IIIa receptors on the surface of platelets and does not significantly interfere with the ability of arginine-glycine-aspartic acid to bind with GPIIb/IIIa. Examples of suitable moieties include alkyl groups and polyglycol groups.

The mixture produced is agitated for a period of time sufficient to allow the platelet GPIIb/IIIa receptors to bind with the GPIIb/IIIa receptor ligand on the small polymeric beads and agglutination of the beads to occur. Agitation is preferably supplied mechanically, for example by placing the assay tube on a rocker. The assay tube can be rocked for up to twenty minutes at 5–40 cpm, but preferably about two minutes at about 20 cpm. Alternatively, the mixture produced can be agitated manually, for example by placing the mixture on a glass plate and rotating or by mixing with stick. Manual agitation can be continued for as long as twenty minutes, but preferably for about 2–3 minutes.

Subsequently, the mixture is assessed to determine whether agglutination of the beads has occurred and, optionally, the extent of the agglutination. Lack of agglutination of the beads indicates that the GPIIb/IIIa receptors on the platelets in the sample are blocked, i.e., greater than about 80% of the GPIIb/IIIa receptors are blocked. Lack of agglutination also indicates that the individual being assessed will have prolonged bleeding times due to about 80% or greater GPIIb/IIIa blockade.

Agglutination of the beads indicates that less than about 80% of GPIIb/IIIa receptors on the platelets in the sample are blocked. The extent of agglutination is indicative of the level of blocked GPIIb/IIIa receptors. A normal level of agglutination indicates that less than about 40–50% of the individual's GPIIb/IIIa receptors are blocked and that the individual will have a normal or near-normal bleeding time. A level of agglutination that is less than normal indicates that between about 50% and about 80% of the individual's GPIIb/IIIa receptors are blocked, and that the individual will have a mild to moderately prolonged bleeding time, i.e., a bleeding time that is longer than normal but less than about thirty minutes. Whether agglutination is less than normal is determined by comparing the amount of agglutination from the blood of an individual being assessed with the amount of agglutination from a standard or control. The standard or control is the amount of agglutination that results from the blood of an individual with a normal platelet count (150,000–350,000 platelets/µl) whose GPIIb/IIIa receptors are more than about 60% unblocked. The standard or control can be predetermined or run simultaneously.

Agglutination is determined visually by whether the beads clump, which is indicative of agglutination, or whether they remain suspended in the solution, which is indicative of the absence of agglutination. Optionally, the beads can be colored to aid in visualizing agglutination, or clumping, of the beads. The level of agglutination is also determined visually by comparing whether there is less clumping in the solution compared with the control or standard.

In the method of the present invention, a thrombin receptor activating peptide is optionally combined with the mixture of anticoagulated blood, buffer and small polymeric beads to which a GPIIb/IIIa receptor ligand is bound or adsorbed. The thrombin receptor is a transmembrane protein that is present in platelets (Vu et al. *Cell* 64:1057 (1992)). A thrombin receptor activator, as defined herein, is a peptide, protein, antibody or small organic molecule that induces platelet activation via the thrombin receptor, i.e., which increases the rate of agglutination when platelets whose GPIIb/IIIa receptors are not blocked when the platelets are combined with a GPIIb/IIIa receptor ligand bound to solid surfaces. A suitable peptide is any peptide of appropriate sequence and size to activate platelets, as described above. The peptide can comprise thrombin, or a portion thereof, such that the amino acid sequence of the peptide or peptide mimic result in activation of the platelets. Vu et al. identified the amino acid sequence of the thrombin receptor and proposed a mechanism of thrombin receptor activation. Thrombin cleaves the thrombin receptor protein, releasing a short receptor fragment and leaving a new amino terminal peptide on the platelet surface. The new amino terminal peptide activates the receptor by functioning as a tethered ligand that interacts with another region of the receptor to induce activation signals. A fourteen amino acid peptide (T-14) (SEQ ID NO: 1) corresponding to the new N-terminus of the cleaved receptor protein is capable of aggregating platelets directly without prior thrombin cleavage (Vu et al.). However, the entire peptide is not required for activity because an eleven amino acid peptide (T-11) (SEQ I.D. NO: 2) lacking the three C-terminal amino acids of T-14 is twice as potent as T-14 (see Coller et al. *Biochemistry* 31:11713 (1992), the contents of which are hereby incorporated by reference into this application in their entirety). A peptide comprising the first five or six amino acids has also been shown to be active. (Vassallo et al., *J. Biol. Chem.* 267: 6081 (1992), Hui et al., *Biochem. Biophys. Res. Commun.* 184:790 (1992), Sabo et al., *Biochem. Biophys.. Res. Commun.* 188:604 (1992) and Scarborough et al., *J. Biol. Chem.* 267:13146 (1992)). In fact, T-6 (SEQ ID NO: 4) has been shown to be more active than the longer T-11 amino acid of SEQ ID NO:2, with the latter having ~20% of the platelet activation activity of T-6. (U.S. Pat. No. 5,455,228 (Coller)).

An important application of the assay of the present invention is for rapid monitoring of an individual during a medical procedure or to determine whether an individual is ready to undergo a medical procedure. This type of monitoring is referred to as "bedside monitoring." For example, monoclonal antibody c7E3 is given prior to angioplasty or atherectomy in high-risk clinical situations to reduce the risk of ischemic complications (The EPIC Investigators, *N.E. J. of Medicine* 330: 956 (1994)). Monoclonal antibody c7E3 acts by blockading the GPIIb/IIIa receptor. Because GPIIb/IIIa blockade inhibits platelet thrombus formation, it is important that blockade of this receptor be reversed prior to invasive surgery in the event that invasive surgery is needed following c7E3 Fab injection. It is advantageous to have an assay that accurately and rapidly determines the extent to which GPIIb/IIIa platelet receptors in the patient's blood are blocked and, thus, the likelihood excessive bleeding will occur. When GPIIb/IIIa blockade is achieved, the patient is ready to undergo the procedure. The addition of a thrombin-activating peptide or other thrombin-activating agent has the advantage of inducing platelet activation, thereby increasing the rate at which the beads of the assay of the present invention agglutinate and, thus, decreasing the time required for the assay to be carried out.

The N-terminal serine group of the thrombin receptor activating peptides, e.g., T-11, T-6, and T-14 (SEQ ID NO:7), is essential to these peptides' ability to induce platelet aggregation. This is based on the observation that acetylation of the N-terminal serine of T-11 results in loss of aggregating ability. In addition, T-11 and T14 lose their ability to induce aggregation when incubated in plasma, because aminopeptidase M, present in plasma, cleaves the N-terminal. Significant losses of platelet aggregating ability can occur in as little as ten minutes (Coller et al., *Biochemistry* 31:11713 (1992)). The platelet aggregating activity of T-6 (SEQ ID NO:4) was shown to decrease within 15 minutes of incubation in plasma and was nearly lost after 60 minutes (U.S. Pat. No. 5,455,228 (Coller)). The presence of aminopeptidase M in whole blood can result in variability in the amount of time required for agglutination of the beads in the assay of the present invention.

The variability in the time required for agglutination can be avoided by carrying out the present method under conditions wherein the cleavage of the N-terminal serine of the thrombin receptor activating peptide is suppressed. This can be accomplished by employing a thrombin receptor activating peptide that is resistant to degradation by aminopeptidase M. A resistant thrombin receptor activating peptide should have the additional property of retaining sufficient activity such that when the resistant thrombin receptor activating peptide is added to the assay of the claimed invention, as described above, agglutination is rapid enough, when the platelet GPIIb/IIIa receptors are not blocked, that the assay can be used for bedside monitoring. An assay suitable for bedside monitoring results in agglutination in less than ten minutes, but preferably in less than five minutes. A preferred thrombin receptor activating peptide that is resistant to degradation by aminopeptidase M is racemic isoSer-Phe-Leu-Leu-Arg-Asn (SEQ ID NO: 3). This peptide is hereinafter referred to as T-6'. Isoserine is an isomer of serine having the formula $NH_2CH_2CHOHCOOH$. The C-2 position of isoserine is chiral, and racemic isoserine is a mixture of D and L isomers. One or both of the isomers is active. T-6' retains 15–20% of the activity of the six amino acid thrombin receptor activating peptide Ser-Phe-Leu-Leu-Arg-Asn (SEQ ID NO. 4) while showing no significant loss of activity after two hours of incubation with platelet poor plasma (see Coller and Prestwich, U.S. Pat. No. 5,455,228, and Coller et al., *J. Biol. Chem.* 268:20741 (1993)), the contents of which are hereby expressly incorporated in their entirety into this application by reference). Other suitable thrombin receptor activating peptides that are resistant to aminopeptidase M include peptides comprising an N-terminus having the amino acid sequence of T-6', such that the peptide is resistant to aminopeptidase M degradation and retains sufficient platelet activating activity, as described above. Examples include analogues of T-11 (SEQ ID NO: 5)

and T-14 (SEQ ID NO: 6), wherein the N-terminal serine of T-11 or T-14 is substituted with iso-serine. Although Applicant does not wish to be bound by any particular mechanism, it is believed that these peptides are resistant to inactivation by aminopeptidase M because isoserine is not cleaved from the N-terminus. Specific requirements for each group of the aminopeptidase M resistant peptides have been determined. $R_1$ may be isoserine, 2,3-diaminopropanoate or 2,3-dihydroxypropanoate. $R_2$ may be any hydrophobic amino acid residue having a cyclic or aromatic group. Preferred amino acids for $R_2$ are phenylalanine, p-benzoylphenylalanine, p-fluorophenylalanine, and p-methylphenylalanine. $R_3$ may be any hydrophobic amino acid such as alanine, phenylalanine, glycine, isoleucine, leucine, methionine, proline, serine, threonine, tryptophan and valine. Preferred are leucine, phenylalanine, and alanine, and most preferred is leucine. $R_4$ may be any hydrophobic amino acid such as those listed for $R_3$. Preferred are leucine, and alanine, and most preferred is leucine. Each of $R_5$ through $R_{14}$ may be absent or, if present, is an L-amino acid with the terminal amino acid being a carboxy or carboxamide, or a moiety that enhances cell penetrating ability of the polypeptide. Such moieties are known in the art and include lipids, steroids, long chain amine's such as decylamine, and sugars such as conjugates of glucosamine, glucuronic acid, etc. Preferred $R_5$ amino acids are arginine and alanine, and most preferred is arginine, and preferred $R_6$ is asparagine. The present invention also encompasses other thrombin. receptor activating peptides such as analogues of T-14, T-11, the 6-mer of T-14 and the 5-mer of T-14 (SEQ ID NO:8) in which the N-terminal serine is substituted with a moiety, preferably an amino acid, that results in resistance of the peptide to cleavage by aminopeptidase M. Also encompassed are peptide stereochemical varieties with resistance to aminopeptidase M. While T-11 with an N-terminal serine group in the D-configuration has only minimal aggregating activity, it has been shown to retain more than half its aggregating activity when incubated in plasma for 1 hour (U.S. Pat. 5,455,228 (Coller)). Suitable thrombin receptor activating peptides can be prepared by peptide synthesis, according to methods known to those skilled in the art (See Example 3).

Alternatively, the variability can be avoided by including an inhibitor of aminopeptidase M in the assay. A suitable inhibitor of aminopeptidase M includes amastatin, which has been shown to enhance platelet aggregation in the presence of aminopeptidase M (Coller et al., *Biochemistry* 31:11713 (1992)). Acetylation of the N-terminus of the thrombin receptor peptide ligand is the traditional method for producing a peptide that resists cleavage by aminopeptidase M, but acetylation of this ligand eliminates receptor activator activity. Other platelet-activators can be used in place of the thrombin receptor activating peptides described above. For example, adenosine diphosphate, collagen, ristocetin, botrocetin, epinephrine, arachidonic acid and its metabolites including thromboxane $A_2$, platelet activating factor, plasmin, serotonin, vasopressin, tissue plasminogen activator, streptokinase and immune complexes can be added, alone or in combination with other platelet activators, to increase the rate of agglutination of the beads in the assay of the present invention. Additionally, application of high levels of shear stress, and artificial surfaces such as those used clinically for prosthetic materials can also activate platelets (Coller, Platelet Morphology, Biochemistry, and Function, 1185).

A preferred embodiment of the present invention is based on the discovery that as a consequence of platelet activation by a thrombin receptor activating peptide, such as T-6', the time period required for agglutination of the small beads is rapid enough for bedside monitoring and is reproducible when the amounts of reagents and the percentage of blocked GPIIb/IIIa receptors in the blood being tested remain constant. For example, 70 $\mu$l of small beads bound with fibrinogen in the presence of 100 $\mu$l buffer (0.01M HEPES, 0.15M, NaCl, 0.5 mM CaCl2), 70 $\mu$l anticoagulated whole blood and 5–10 $\mu$l T-6' (see Example 5) will agglutinate in two minutes if high grade GPIIb/IIIa blockade has not been achieved, i.e. when less than 80% of the GPIIb/IIIa receptors are blocked. The concentration of T-6' in this assay can generally range from between about 2–5 $\mu$M, which allows variations in the amounts of the other reagents. The skilled artisan can readily determine such variations. This provides a quick and simple-assay that can be performed at the bedside to determine when a patient undergoing antiplatelet therapy has achieved GPIIb/IIIa blockade.

A bedside assay for GPIIb/IIIa can be used in conjunction with a variety of other medical procedures, for which levels of GPIIb/IIIa blockade may differ. For example, platelet transfusions may be needed prior to invasive surgery in order to prevent excessive bleeding if GPIIb/IIIa blockade is greater than 50% (Coller et al. *N.Y. Acad. Sci.*, 614:193 (1993)). Determining whether GPIIb/IIIa receptor blockade has returned to normal levels is particularly important if invasive surgery is needed immediately after a procedure such as angioplasty or atherectomy, in which the GPIIb/IIIa blockade has been elevated by antiplatelet therapy. Another embodiment refers to an assay to determine when 50% or less of the GPII/IIIa receptors of an individual are blocked. The same quantities of reagents are used as with the assay for determining 80% blockade, as discussed above, except that the concentration of isoSer-Phe-Leu-Leu-Arg-Asn is reduced to about 0.2–1 $\mu$M. Agglutination within two minutes indicates that the individual will have a normal or near normal bleeding time. Less than about 50% of the GPIIb/IIIa receptors are blocked in this individual.

Assays that are indicative of different levels of GPIIb/IIIa blockade can be readily determined by one of ordinary skill in the art. Whole blood is drawn from an individual with a normal platelet count, (150,000–300,000 platelets/$\mu$l) in whom a known percentage of GPIIb/IIIa receptors are blocked. The amounts of reagents used in the assay, i.e. anticoagulated blood with the known percentage of GPIIb/IIIa blockade, buffer, small beads and T-6' or other platelet activator can be varied until a ratio of reagents is found that results in agglutination within a convenient period of time. Generally, it is most convenient to vary the amount of thrombin receptor activator in order to obtain an assay in which agglutinization occurs within a desired period of time for a certain level of GPIIb/IIIa blockade. The percentage of GPIIb/IIIa receptors in the blood that are blocked can be determined by methods known to those skilled in the art, e.g. radiolabeled 7E3 binding (Coller et al., *N. Y. Acad. Sci.*, 614:193 (1993)) or flow cytometry (Coller et al. *Blood* 74:182, (1989)). This ratio of reagents can be used in the assay of the present invention to test the extent of GPIIb/IIIa blockade in a patient in whom the extent of GPIIb/IIIa blockade is unknown. Agglutination of the beads within the desired period of time indicates that extent of GPIIb/IIIa blockade is less than or equal to the indicated percentage. Failure of the beads to agglutinate indicates that GPIIb/IIIa blockade equals or exceeds the indicated percentage. If the platelet count is abnormally low, there may be no agglutination, even with there being relatively little receptor blockade. It is necessary to perform a platelet count to know that it is normal (150,000–350,000/$\mu$l).

A kit is provided herein, in which the reagents necessary for carrying out the assay of the present invention are provided. The kit comprises a blood vial, a buffer that maintains the pH and salt concentration of the blood sample assessed within ranges suitable for platelet mediated agglutination of the solid surface and small polymeric beads coated with platelet GP IIb/IIIa receptor ligand. The buffer can be in solution, or can consist solely of the buffering composition and salts. The buffering composition and salts may be added directly to the blood sample to avoid dilution of the blood, or added as a solution after being combined with a known amount of water to give the desired buffer solution. optionally, the kit can also comprise an anticoagulant. In one embodiment, the preferred buffer is HEPES; the anticoagulant is citrate; a GPIIb/IIIa receptor ligand is fibrinogen; small polymeric beads are polyacrylonitrile or carboxylated polystyrene in which a peptide GPIIb/IIIa receptor ligand, such as fibrinogen, is covalently bonded to the bead surface by means of a covalent bond between the N-terminus of the peptide and an N-hydroxysuccinimide or carboxylate group on the bead surface.

In a further embodiment, the kit additionally comprises a platelet activator, such as a thrombin receptor activating peptide. For example, the thrombin receptor activating peptide is isoSer-Phe-Leu-Leu-Arg-Asp. If the thrombin receptor activating peptide is not resistant to degradation by aminopeptidase M, the kit can additionally comprise an inhibitor of aminopeptidase M, such as amastatin.

As discussed above, it is advantageous for certain applications of the present invention that the assay of the present invention be used for bedside monitoring and that the assay indicate whether a certain level of GPIIb/IIIa receptor blockade has been achieved. As discussed earlier, the relative amounts of reagents can be adjusted so that agglutination of the beads results within a desired period of time if the desired level of GPIIb/IIIa receptor blockade is not achieved. A kit to be used in this context generally contains the quantity of buffer, thrombin receptor activating peptide, such as isoSer-Phe-Leu-Leu-Arg-Asp, and GPIIb/IIIa ligand-coated polymeric beads such that agglutination of the beads will result within a known period of time suitable for bedside monitoring when mixed with a pre-determined amount of anticoagulated whole blood in which the desired level of GPIIb/IIIa receptor blockade has not been achieved. For example, if the method is to be carried out in approximately two minutes and it is to be determined whether the level of GPIIb/IIIa blockade is 80% or less, the kit comprises 100 parts by volume buffer to 10 parts by volume beads to 5–10 parts by volume isoSer-Phe-LeuLeu-Arg-Asp. In another aspect, the desired period of time is two minutes and the level of GPIIb/IIIa- blockade is 50% or less.

Another embodiment of the present invention refers to a method of diagnosing individuals with bleeding abnormalities due to reduced levels of unblocked GPIIb/IIIa receptors. For example, individuals who are homozygous for Glanzmann thrombasthenia have virtually no functional GPIIb/IIIa receptors and consequently have prolonged bleeding times. Individuals who are heterozygous for Glanzmann thrombasthenia haves 50–60% of the normal number of GPIIb/IIIa receptors, but show normal bleeding times (Coller et al. *Ann. N.Y. Acad. Sci.* 614:193 (1993)). Individuals with platelet levels below about 100,000 platelets/$\mu$l are severely thrombocytopenic and also have prolonged bleeding times. Consequently, when the blood of an individual who has not been administered an agent that blocks GPIIb/IIIa receptor and who is homozygous for Glanzmann thrombasthenia or is severely thrombocytopenic or has other platelet function defects is tested for "blockade" of GPIIb/IIIa receptors by the assay of the present invention, no agglutination of the beads will be observed. The method of detecting an individual who is homozygous for Glanzmann thrombasthenia, or has other platelet function defects, or is thrombocytopenic comprises testing the blood of the individual for GPIIb/IIIa blockade by the assay described herein. The blood of the individual should be tested when the individual has not been administered an agent, e.g., an agent used for antiplatelet therapy, that blocks GPIIb/IIIa receptors. The absence of agglutination of the beads indicates that the individual should be tested further for Glanzmann thrombasthenia, other platelet function defects or thrombocytopenia.

The invention is further illustrated by the following examples, which are not intended to be limiting in any way.

EXEMPLIFICATION

EXAMPLE 1

Preparation of Fibrinogen Coated Carboxylated Polystyrene Beads 0.5 ml of 2.5% carboxylated microparticles obtained from Polysciences Incorporated were placed into an Eppendorf centrifuge tube having a capacity of 1.5–1.9 ml. A sufficient amount of 0.1M carbonate buffer, pH 9.6, was added to fill the tubes, which was then centrifuged for 56 minutes in a micro-centrifuge. The supernatant was carefully removed using a pasteur pipette and discarded. The pellet was then resuspended in carbonate buffer. To resuspend the pellet, the tube was filled halfway, capped, vortexed and then filled to capacity. The tube was then recentrifuged for 5–6 minutes and the supernatant removed and discarded. The pellet was then resuspended in 0.02M sodium phosphate buffer, pH 4.5, and centrifuged for 5–6 minutes. The supernatant was then removed and discarded. The resuspension in phosphate buffer and centrifugation was repeated two more times, after which the supernatant was removed and discarded.

A 2% solution of 1-(3-dimethylaminopropyl)-3-ethyl carbodiimide hydrochloride dissolved in 0.02M sodium phosphate (2% carbodiimide) buffer was freshly prepared within 15 minutes of using. 0.625 ml of this 2% carbodiimide solution was added dropwise to the pellet. The resulting suspension was mixed for 3–4 hours at room temperature using an end-to-end mixture. The suspension was then centrifuged for 5–6 minutes and the supernatant was removed and discarded. The resulting pellet was resuspended in 0.02M phosphate buffer and centrifuged for 5–6 minutes. The supernatant was then removed and discarded. This process of resuspending in phosphate buffer and centrifuging was repeated two more times.

The resulting pellet was suspended in 0.2M borate buffer, pH 8.5. 300 $\mu$g of fibrinogen was added to the suspension, which was then gently mixed overnight at room temperature on an end-to-end mixer. 50 $\mu$l of 0.5M ethanolamine was then added and the suspension mixed for 30 minutes.

The suspension was then centrifuged for 10 minutes, and the supernatant was removed and discarded. The pellet was then resuspended in 1 ml of 10 mg per milliliter BSA solution in borate buffer. The mixture was capped, vortexed and then gently mixed for 30 minutes at room temperature. After centrifuging for 5–6 minutes the supernatant is removed and discarded. This process of resuspending the pellet in BSA solution and centrifuging was repeated one time. The supernatant was then removed and discarded, and the pellet resuspended in 0.5 ml of PBS, pH 7.4, containing 10 mg per milliliter BSA, 5% glycerol, and 0.1% NaN$_3$, and stored at 4° C.

The extent of coupling was monitored by immunologic fibrinogen determination, optical density at 280 nm and or protein assays (Lowry or Bio-Rad Protein Assay).

EXAMPLE 2

Covalent Coupling of Fibrinogen to Polymerized Acrylonitrile

Solid beads of polymerized acrylonitrile, primarily 1–3 μm in diameter, with free carboxyl groups and N-hydroxysuccinimide groups on their surface (Matrex 102, Amicon Corporation) come packed in dioxane to prevent hydrolysis of the esters. One milliliter of a well mixed suspension (containing 67 mg of beads) was centrifuged at 10,000 g for 1 minute, the supernatant dioxane removed, and the beads rapidly washed twice with 1.2 ml of 0.01M Na acetate, pH 6. The dried, washed beads were then resuspended in 1.5 ml of either fibrinogen or albumin (2 mg/ml) solution in 0.03M sodium citrate, pH 7.5, and allowed to rock overnight at 4° C. In some experiments, a smaller volume of a more dilute protein solution (0.7 mg/ml) was employed, but the same ratio of total protein to beads (0.045) was always maintained. The extent of coupling was monitored by immunologic fibrinogen determination, optical density at 280 nm and/or protein assays (Lowry or Bio-Rad Protein Assay) on the postcoupling supernatant after dialysis (to remove the interfering chromophore released by the reaction). In 8 experiments, the fibrinogen coupled with 88%–100% efficiency, whereas in 4 experiments, the albumin coupled at 17%–27% efficiency. Since complete coupling of fibrinogen required only ~0.1% of the total reactive sites, the reaction proceeded very rapidly and was complete in less than 7 minutes. Calculations based on the manufacturer's estimate of the surface area of the beads (6 sq. m/g) indicate that there is approximately 1 molecule of fibrinogen every 8000 square Å of bead surface, which translates into approximately 1 molecule of fibrinogen every 90 Å. On average, there were ~500, 000 fibrinogen molecules coupled to each bead. When adjusted for the difference in molecular weight, virtually the same number of albumin molecules were bound to the beads as were fibrinogen molecules. After the coupling procedure was completed, the beads were washed extensively with 0.15M NaCl, 0.01M Tris-HCL, 0.05% azide, pH 7.4 until the supernatant buffer's absorbance at 280 nm reached baseline so as to remove the products of the reaction and any nonspecifically absorbed fibrinogen. Both the fibrinogen and albumin beads were then resuspended in equal volumes of buffer (2–4 ml), giving a particle count of ~250,000/μl. To assess the amount of fibrinogen that adsorbed to the beads instead of being covalently coupled, beads were suspended in a solution of 3% SDS 8M urea, 0.02M NaPO for 30 minutes at 37° C., and the protein content in the solution determined. Less than 2' of the bound protein could be eluted in this way.

EXAMPLE 3

Synthesis of Thrombin Receptor Activating Peptides

This example describes synthesis of thrombin receptor activating peptides, T-11, T-14 and T-6'. The methods described can be used to produce other thrombin receptor activating peptides. T-14 and T-11 were prepared on an automated peptide synthesizer (Applied Biosystems 430A; Foster° City, Calif.) using t-Boc chemistry, 4-methylbenzhydrylamine resins and N-methylpyrrolidone as the coupling solvent as previously described (Beer et al., Blood, 79: 117 (1992)). The protecting groups were β-benzyl ester for aspartic acid, benzyl for serine, 2-bromobenzyloxycarbonyl for tyrosine, 2-chlorobenzyloxycarbonyl for lysine, and tosyl for arginine. Arginine, asparagine, tyrosine, and selected proline and phenylalanine residues were double-coupled. Dimethylsulfoxide and anisole were included in all of the hydrogen fluoride cleavage solutions. Peptides were assessed by reverse-phase HPLC and selected peptides were purified by this technique. Acetylation of the N-terminus of Tell to form Ac-T-11 was accomplished with acetic anhydride prior to cleavage from the resin. The mass of selected peptides was determined by fast atom bombardment mass spectrometry as previously described (Beer et al. 1992). T-6' was prepared by first synthesizing the peptide Phe-Leu-Leu-Arg-Asp by the automated method as described in the previous paragraph and then manually adding the t-butoxycarbonyl racemic isoserine in dichloromethane and dimethylformamide (2:1) to the peptide on the resin using 1-hydroxybenzotriazole to activate the isoserine and N,N'-diisopropylcarbodiimide to couple it to the peptide. The peptide was then cleaved from the resin as described in the previous paragraph.

EXAMPLE 4

Rapid Whole Blood Assay for Determining Blockade of Platelet Glycoprotein IIb/IIIa Receptors Blood (9 volumes) is drawn from a patient by syringe and placed in a standard blue-top tube containing sodium citrate (1 volume of 3.8% sodium citrate). Alternatively, blood may be drawn by vacutainer directly into a blue-top tube. The tube is then inverted to mix the anticoagulant with the whole blood. Then 50 μl of this mixture is added to 50 μl of buffer (0.15M NaCl, 0.5 mM CaCl$_2$, 0.05M HEPES, pH 7.4) and to 5 μl of fibrinogen coated beads prepared by the method of Example 2. The mixture is rotated on a glass plate for about two minutes. If GPIIb/IIIa receptors are blocked, the beads remain in suspension. If the GPIIb/IIIa receptors are not blocked, the platelets interact with the fibrinogen bound to the surface of the beads, resulting in clumping of the beads.

EXAMPLE 5

Rapid Whole Blood Assay for Determining Whether 80% of Glycoprotein IIb/IIIa is Blocked Blood (9 volumes) is drawn from a patient by syringe and placed into standard blue-top tube containing sodium citrate (1 volume of 3.8% sodium citrate). Alternatively, blood may be drawn by Vacutainer directly into a blue-top tube. The tube is then inverted to mix the anticoagulant with the whole blood. Then 70 μl of this mixture is added to an assay tube containing 100 μl of buffer (0.15M NaCl, 0.5 mM CaCl$_2$, 0.01M HEPES, pH 7.4), 10 μl of well-mixed fibrinogen coated beads prepared by the method of Example 1, and 5–10 pl of isoSer-Phe-Leu-Leu-Arg-Asn (SEQ ID NO:3).

The assay tube is then placed on a rocker and rocked at 20 cpm at room temperature for two minutes. The tube is removed from the rocker, held vertically to allow the blood to drain and viewed. If less than 80% of GPIIb/IIIa receptor blockade has been achieved in the patient's blood, agglutinated beads are readily seen in the streak marking where the blood tilted back and forth. If greater than 80% of GPIIb/IIIa receptor blockade has been achieved in the patient's blood, the streak does not contain bead agglutinates.

EXAMPLE 6

Correlation of Agglutination to GPIIb/IIIa Blockade

Purified peak I-2 fibrinogen is coupled to 3 µm, blue carboxylated beads (obtained from Polysciences, Inc.) using a water soluble carbodiimide (EDC) by the method of Example 1. The assay is conducted by adding to a 12×75 mm glass test tube: 100 µl of buffer, 20 µl of beads (2.5% slurry), and 5 µl of isoSer-Phe-Leu-Leu-Arg-Asn. Blood is collected into citrate anticoagulant and 70 µl of the whole blood is added to the test tube, which is then capped, placed on a rocking platform, and rocked at 16 cycles/min. When normal blood was tested using 1 or 2 µM activating peptide, a 4+ agglutination endpoint was easily observed in all donors (n=10) by 2 min. Pretreating the blood with c7E3 Fab at 5 doses between 0.8–3.0 µg/ml for about 10 minutes at 22° C. produced increasing GPIIb/IIIa receptor blockade and elimination of agglutination. Using 2 µM activating peptide, the assay remained positive (i.e., 1–4+) at c7E3 Fab concentrations of 0.8 (n=1), 1.2 (n=1), 1.5 (n=3), and 1.8 (n=2) µg/ml, corresponding to GPIIb/IIIa receptor blockade of 56%; 77%; 68, 68, and 82%; and 66 and 73%. The assay became negative (i.e., 0+) at c7E3 Fab concentrations of 1.2 (n=1), 1.5 (n=1), 1.8 (n=3) and 2.4 (n=2) µg/ml, corresponding to GPIIb/IIIa receptor blockade of 77%; 92%; 83, 88 and 94%; and 88 and 89%. Aspirin (1 mM) and/or heparin (3.5 U/ml) did not appreciably affect the results. The percentage of receptor blockade was assayed by radiolabeled 7E3 binding as reported in Coller et al., *N.Y. Acad. Sci.*, 614:193 (1993).

EQUIVALENTS

Those skilled in the art will know, or be able to ascertain using no more than routine experimentation, many equivalents to the specific embodiments of the invention described herein. These and all other equivalents are intended to be encompassed by the following claims.

What is claimed is:

1. A method of determining whether an individual has reduced ability to form platelet thrombi, comprising the steps of:
   a) obtaining a blood sample from the individual being assessed;
   b) mixing the blood sample with 1) an anticoagulant; 2) sufficient buffer to maintain the pH and salt concentration of the anticoagulated blood within a range suitable for platelet aggregation; 3) a platelet GPIIb/IIIa receptor ligand immobilized on a solid surface and 4) a platelet aggregation activator;
   c) agitating the mixture formed in b) for a period of time sufficient for unblocked platelet GPIIb/IIIa receptors to bind with the platelet GPIIb/IIIa receptor ligands on said solid surface; and
   d) assessing platelet-mediated agglutination in the agitated mixture, wherein the absence of agglutination indicates that the individual has reduced ability to form platelet thrombi.

2. The method of claim 1 wherein the GPIIb/IIIa receptor ligand is selected from the group consisting of fibrinogen, monoclonal antibody lOE5, monoclonal antibody c7E3, von Willebrand factor, fibronectin, vitronectin, and synthetic ligands having an arginine-glycine-aspartic acid (RGD) GPIIb/IIIa binding sequence.

3. The method of claim 1 wherein the platelet aggregation activator is selected from the group of adenosine diphosphate, collagen, ristocetin, botrocetin, epinephrine, arachidonic acid and its metabolites, platelet activating factor, plasmin, serotonin, vasopressin, tissue plasminogen activator, streptokinase and immune complexes.

4. The method of claim 3 wherein the arachidonic acid metabolite comprises thromboxane $A_2$.

5. The method of claim 1 wherein the solid surface comprises small glass or polymeric beads, the surface of said beads modified with a GPIIb/IIIa receptor ligand.

6. The method of claim 5 wherein the small polymeric beads have diameters from about 1 to about 6 $\mu$m.

7. The method of claim 5 wherein the small polymeric beads comprise carboxylated polystyrene or carboxylated polyacrylonitrile beads.

8. A method of determining the degree of GPIIb/IIIa receptor blockade in a blood sample, comprising the steps of:
   a) obtaining a blood sample from an individual being assessed;
   b) mixing the blood sample with 1) an anticoagulant; 2) sufficient buffer to maintain the pH and salt concentration of the anticoagulated blood within a range suitable for platelet aggregation; 3) a platelet GPIIb/IIIa receptor ligand immobilized on a solid surface and 4) a platelet aggregation activator;

c) agitating the mixture formed in b) for a period of time sufficient for unblocked platelet GPIIb/IIIa receptors to bind with the platelet GPIIb/IIIa receptor ligands on said solid surface; and d) assessing platelet-mediated agglutination in the agitated mixture, wherein the absence of agglutination indicates that about 80% or more of the GPIIb/IIIa receptors are blocked, and the presence of normal agglutination indicates that less than about 50% of the GPIIb/IIIa receptors are blocked.

9. The method of claim 8 wherein the GPIIb/IIIa receptor ligand is selected from the group consisting of fibrinogen, monoclonal antibody 1OE5, monoclonal antibody c7E3, von Willebrand factor, fibronectin, vitronectin, and synthetic ligands having an arginine-glycine-aspartic acid (RGD), or RGD functional equivalent GPIIb/IIIa binding sequence.

10. The method of claim 8 wherein the platelet aggregation activator is selected from the group of adenosine diphosphate, collagen, ristocetin, botrocetin, epinephrine, arachidonic acid and its metabolites, platelet activating factor, plasmin, serotonin, vasopressin, tissue plasminogen activator, streptokinase and immune complexes.

11. The method of claim 10 wherein the arachidonic acid metabolite comprises thromboxane $A_2$.

12. The method of claim 8 wherein the platelet aggregation activator comprises an N-terminal isoSer, 2,3-diaminopropanoate, or 2,3-dihydroxypropanoate thrombin receptor activating peptide.

13. The method of claim 8 wherein the solid surface comprises small glass or polymeric beads, the surface of said beads modified with a GPIIb/IIIa receptor ligand.

14. The method of claim 13 wherein the small polymeric beads have diameters from about 1 to about 6 $\mu$m.

15. The method of claim 13 wherein the small polymeric beads comprise carboxylated polystyrene or carboxylated polyacrylonitrile beads.

16. A method of diagnosing Glanzmann thrombasthenia, other platelet function defects, or thrombocytopenia in an individual, comprising the steps of:

a) obtaining a blood sample from an individual being assessed for Glanzmann thrombasthenia, other platelet function defects, or thrombocytopenia at a time when the individual has not been administered an agent that blocks platelet GPIIb/IIIa receptors;

b) mixing the blood sample with 1) an anticoagulant; 2) sufficient buffer to maintain the pH and salt concentration of the anticoagulated blood within a range suitable for platelet aggregation; and 3) a platelet GPIIb/IIIa receptor ligand immobilized on a solid surface;

c) agitating the mixture formed in b) for a period of time sufficient for unblocked platelet GPIIb/IIIa receptors to bind with the platelet GPIIb/IIIa receptor ligands on said solid surface; and d) assessing platelet-mediated agglutination in the agitated mixture, wherein the absence of agglutination is indicative of Glanzmann thrombasthenia, other platelet function defects, or thrombocytopenia.

17. The method of claim 16 wherein the GPIIb/IIIa receptor ligand is selected from the group consisting of fibrinogen, monoclonal antibody 1OE5, monoclonal antibody c7E3, von Willebrand factor, fibronectin, vitronectin, and synthetic ligands having an arginine-glycine-aspartic acid (RGD) or RGD functionally equivalent GPIIb/IIIa binding sequence.

18. The method of claim 16 further comprising the addition of a platelet aggregation activator in step b).

19. The method of claim 18 wherein the platelet aggregation activator is selected from the group of adenosine diphosphate, collagen, ristocetin, botrocetin, epinephrine, arachidonic acid and its metabolites, platelet activating factor, plasmin, serotonin, vasopressin, tissue plasminogen activator, streptokinase and immune complexes.

20. The method of claim 19 wherein the arachidonic acid metabolite comprises thromboxane $A_2$.

21. The method of claim 18 wherein the platelet aggregation activator is a thrombin receptor activator.

22. The method of claim 21 wherein the thrombin receptor activator is a thrombin receptor activating peptide.

23. The method of claim 22 further comprising adding a plasma aminopeptidase M inhibitor to the mixture of blood, anticoagulant, buffer, GPIIb/IIIa receptor ligand, and thrombin receptor activating peptide.

24. The method of claim 22 wherein the thrombin receptor activating peptide is selected from the group consisting of (SEQ ID NOS: 1, 2, 4 and 7).

25. The method of claim 24 further comprising adding a plasma aminopeptidase M inhibitor to the mixture of blood, anticoagulant, buffer, GPIIb/IIIa receptor ligand, and thrombin receptor activating peptide.

26. The method of claim 22 wherein the thrombin receptor activating peptide comprises a peptide resistant to inactivation by plasma aminopeptidase M.

27. The method of claim 26 wherein the thrombin receptor activating peptide comprises an N-terminal isoSer, 2,3-diaminopropanoate, or 2,3-dihydroxypropanoate peptide.

28. The method of claim 27 wherein the thrombin receptor activating peptide comprises at least 5 but no more than about 14 amino acids, wherein: $R_1$ is selected from the group consisting of isoserine, 2,3-diaminopropanoate or 2,3-dihydroxypropanoate; $R_2$ is any hydrophobic amino acid residue having a cyclic or aromatic group; $R_3$ is any hydrophobic amino acid; $R_4$ is any hydrophobic amino acid; each of $R_5$ to $R_{14}$, if present, is an L-amino acid with the terminal amino acid being a carboxy or carboxamide, or a moiety that enhances cell penetrating ability of the polypeptide, the cell penetrating moiety selected from the group consisting of lipids, steroids, long chain amines and sugars.

29. The method of claim 28 wherein: $R_2$ is selected from the group consisting of phenylalanine, p-benzoylphenylalanine, p-fluorophenylalanine, and p-methylphenylalanine; $R_3$ is selected from the group consisting of leucine, phenylalanine, and alanine; $R_4$ is selected from the group consisting of leucine, and alanine; and $R_5$ is selected from the group consisting of arginine, and alanine.

30. The method of claim 29 wherein $R_6$ is asparagine.

31. The method of claim 27 wherein the N-terminal isoSer peptide is selected from the group consisting of (SEQ ID NOS: 3, 5, 6, and 8).

32. The method of claim 31 wherein the N-terminal isoSer peptide comprises isoSer-Phe-Leu-Leu-Arg-Asn (SEQ ID No: 3).

33. The method of claim 16 wherein the solid surface comprises small glass or polymeric beads, the surface of said beads modified with a GPIIb/IIIa receptor ligand.

34. The method of claim 33 wherein the small polymeric beads have diameters from about 1 to about 6 $\mu$m.

35. The method of claim 33 wherein the small polymeric beads comprise carboxylated polystyrene or carboxylated polyacrylonitrile beads.

* * * * *